(12) United States Patent
Yokota

(10) Patent No.: US 9,581,802 B2
(45) Date of Patent: *Feb. 28, 2017

(54) ENDOSCOPE DEVICE, AND MEASUREMENT METHOD

(71) Applicant: OLYMPUS CORPORATION, Shibuya-ku, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 532 days.

This patent is subject to a terminal disclaimer.

(21) Appl. No.: 14/085,726

(22) Filed: Nov. 20, 2013

(65) Prior Publication Data

US 2014/0071239 A1     Mar. 13, 2014

Related U.S. Application Data

(63) Continuation of application No. PCT/JP2012/063266, filed on May 24, 2012.

(30) Foreign Application Priority Data

May 24, 2011   (JP) ................ 2011-116141

(51) Int. Cl.
*H04N 13/02*    (2006.01)
*G02B 23/24*    (2006.01)
(Continued)

(52) U.S. Cl.
CPC ........ *G02B 23/2415* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 5,150,254 A   9/1992  Saitou
5,434,669 A   7/1995  Tabata et al.
(Continued)

FOREIGN PATENT DOCUMENTS

EP   2106748 A1   10/2009
EP   2272417 A1    1/2011
(Continued)

OTHER PUBLICATIONS

International Search Report (ISR) dated Jul. 10, 2012 (and English translation thereof) issued in International Application No. PCT/JP2012/063266.

(Continued)

*Primary Examiner* — Mohammed Rahaman
(74) *Attorney, Agent, or Firm* — Holtz, Holtz & Volek PC

(57) ABSTRACT

Provided with an endoscope device configured to measure a specimen using a pattern projection image of the specimen on which a light and shade pattern of light is projected, includes: an imaging unit configured to acquire an image of the specimen; an illumination unit having a first light source configured to emit illumination light to illuminate an observation field of vision of the imaging unit; a pattern projection unit having a second light source configured to emit projection light to project the light and shade pattern on the specimen; a display unit configured to display the image acquired by the imaging unit; and a control unit configured to control the imaging unit, the illumination unit, the pattern projection unit, and the display unit.

12 Claims, 6 Drawing Sheets

(51) Int. Cl.
*G01B 11/25* (2006.01)
*A61B 1/00* (2006.01)
*A61B 1/06* (2006.01)
*A61B 5/107* (2006.01)
*A61B 1/045* (2006.01)

(52) U.S. Cl.
CPC ...... *A61B 1/00066* (2013.01); *A61B 1/00193* (2013.01); *A61B 1/045* (2013.01); *A61B 1/0684* (2013.01); *A61B 5/1077* (2013.01); *A61B 5/1079* (2013.01); *G01B 11/25* (2013.01); *H04N 13/0203* (2013.01); *A61B 1/00052* (2013.01)

(56) References Cited

U.S. PATENT DOCUMENTS

| | | | |
|---|---|---|---|
| 5,784,098 | A | 7/1998 | Shoji et al. |
| 6,464,633 | B1 | 10/2002 | Hosoda et al. |
| 2005/0061062 | A1 | 3/2005 | Kaneko et al. |
| 2009/0225321 | A1* | 9/2009 | Bendall ............ G01B 11/2527 356/447 |
| 2009/0225333 | A1 | 9/2009 | Bendall et al. |
| 2009/0244260 | A1* | 10/2009 | Takahashi .......... A61B 1/00172 348/45 |
| 2010/0063355 | A1* | 3/2010 | Matsuura ............ A61B 1/045 600/109 |
| 2010/0149315 | A1 | 6/2010 | Qu et al. |
| 2011/0267444 | A1* | 11/2011 | Yamaguchi ........ A61B 1/00009 348/65 |
| 2014/0052005 | A1 | 2/2014 | Yokota |
| 2014/0071257 | A1 | 3/2014 | Yokota |

FOREIGN PATENT DOCUMENTS

| | | | |
|---|---|---|---|
| JP | 63200115 | A | 8/1988 |
| JP | 01209415 | A | 8/1989 |
| JP | 02-085706 | A | 3/1990 |
| JP | 02287311 | A | 11/1990 |
| JP | 03128043 | A | 5/1991 |
| JP | 05045132 | A | 2/1993 |
| JP | 05211988 | A | 8/1993 |
| JP | 09-061132 | A | 3/1997 |
| JP | 10-239031 | A | 9/1998 |
| JP | 10-239034 | A | 9/1998 |
| JP | 10104483 | A1 | 10/2002 |
| JP | 2005091265 | A | 4/2005 |
| JP | 2007139822 | A | 6/2007 |
| JP | 2007144024 | A | 6/2007 |
| JP | 2008-229025 | A | 10/2008 |
| JP | 2009019941 | A | 1/2009 |
| JP | 2009061014 | A | 3/2009 |
| JP | 2009240621 | A | 10/2009 |
| JP | 2009258273 | A | 11/2009 |
| WO | 03105289 | A2 | 12/2003 |
| WO | WO 2007/102195 | A1 | 9/2007 |

OTHER PUBLICATIONS

Final Office Action dated Sep. 6, 2016, in U.S. Appl. No. 14/061,530.
Extended European Search Report dated Apr. 15, 2014 in European Application No. 12789379.0.
Extended European Search Report dated May 20, 2014 in European Application No. 12777405.7.
European Office Action dated Apr. 4, 2016, issued in European Application No. 12777405.7.
International Search Report (ISR) dated Jul. 10, 2012, issued in International Application No. PCT/JP2012/063258.
International Search Report (ISR) dated Jul. 24, 2012, issued in International Application No. PCT/JP2012/060832.
Japanese Office Action (and English translation thereof) dated May 7, 2015, issued in Japanese Application No. 2011-099889.
Japanese Office Action (and English translation thereof) dated Mar. 3, 2015, issued in counterpart Japanese Application No. 2011-116141.
U.S. Appl. No. 14/061,530, First Named Inventor: Masayoshi Yokota; Title: "Endoscope Apparatus and Measuring Method"; filed Oct. 23, 2013.
U.S. Appl. No. 14/078,223, First Named Inventor: Masayoshi Yokota; Title: "Endoscope"; filed Nov. 12, 2013.

* cited by examiner

ENDOSCOPE DEVICE, AND MEASUREMENT METHOD

CROSS REFERENCE TO RELATED APPLICATIONS

This application is a continuation application based on a PCT Patent Application No. PCT/JP2012/063266, filed May 24, 2012, whose priority is claimed on Japanese Patent Application No. 2011-116141, filed May 24, 2011, the entire content of which are hereby incorporated by reference.

BACKGROUND OF THE INVENTION

Field of the Invention

The present invention relates an endoscope device and a measurement method, and more particularly, to an endoscope device configured to project a pattern such as stripes or the like on a specimen and measure a 3-dimensional shape of a surface of the specimen, and a method of measuring a 3-dimensional shape of a specimen using the endoscope device.

Description of the Related Art

In the related art, in order to inspect a specimen, an endoscope including a long insertion unit and having an observation unit such as an optical system, an imaging device, or the like, installed at a tip of the insertion unit is used. In such endoscopes, an endoscope device configured to acquire a plurality of stripe images formed by projecting a stripe pattern on a specimen while deviating a phase of the stripe pattern and calculate a 3-dimensional shape of the specimen by a known phase shift method using the plurality of stripe images is already known. For example, US Patent Application, Publication No. 2009/0225321 discloses an endoscope device having two projection windows configured to project stripes and installed at a tip surface of an insertion unit.

SUMMARY

The present invention provides an endoscope device and a measurement method that are capable of determining whether a condition is appropriate for measurement for a short time.

According to a first aspect of the present invention, an endoscope device is configured to measure a specimen using a pattern projection image of the specimen on which a light and shade pattern of light is projected, the endoscope device comprising: an imaging unit configured to acquire an image of the specimen; an illumination unit having a first light source configured to emit illumination light to illuminate an observation field of vision of the imaging unit; a pattern projection unit having a second light source configured to emit projection light to project the light and shade pattern on the specimen; a display unit configured to display the image acquired by the imaging unit; and a control unit configured to control the imaging unit, the illumination unit, the pattern projection unit, and the display unit, wherein the control unit is configured to control the imaging unit to continuously acquire a light field image, which has been obtained by illuminating the illumination light on the specimen, and a pattern projection image, which has been obtained by projecting the light and shade pattern on the specimen, extract the pattern projection image by dividing the pattern projection image from the light field image, and measure a 3-dimensional shape using the pattern projection image that has been extracted.

According to a second aspect of the present invention, in the endoscope device according to the first aspect, the control unit may display a cursor used to determine a region in which the 3-dimensional shape of the specimen is measured in an imaging field of vision of the imaging unit on the display unit, set the region on the display unit based on coordinates of the cursor, and measure the 3-dimensional shape of the corresponding specimen in the region.

According to a third aspect of the present invention, in the endoscope device according to the first aspect, the control unit may measure the 3-dimensional shape of the specimen using only one pattern projection image by at least one of a spatial phase shift method, a Fourier transform method, a stripe order analysis and an optical cutting method.

According to a fourth aspect of the present invention, an endoscope device configured to measure a specimen using a pattern projection image of the specimen on which a light and shade pattern of light is projected, includes: an imaging unit configured to acquire an image of the specimen; an illumination unit having a first light source configured to emit illumination light to illuminate an observation field of vision of the imaging unit; a pattern projection unit having a second light source configured to emit projection light to project the light and shade pattern on the specimen; a display unit configured to display the image acquired by the imaging unit; and a control unit configured to control the imaging unit, the illumination unit, the pattern projection unit, and the display unit. The control unit varies an emission state of the illumination light from the first light source at a predetermined period, reduces emission of the projection light from the second light source in a state in which the illumination light is emitted from the first light source, emits the projection light from the second light source in a state in which emission of the illumination light from the first light source is reduced, allows the imaging unit to acquire a light field image obtained by illuminating the specimen with the illumination light in a state in which the illumination light is emitted from the first light source, allows the imaging unit to acquire the pattern projection image obtained by projecting the light and shade pattern on the specimen in a state in which the projection light is emitted, measures a 3-dimensional shape of the specimen using the pattern projection image acquired by the imaging unit, and displays information obtained by the measurement using the pattern projection image on the display unit with the light field image.

According to a fifth aspect of the present invention, in the endoscope device according to the fourth aspect, the control unit may display a cursor used to determine a region in which the 3-dimensional shape of the specimen is measured in an imaging field of vision of the imaging unit on the display unit, set the region on the display unit based on coordinates of the cursor, and measure the 3-dimensional shape of the corresponding specimen in the region.

According to a sixth aspect of the present invention, in the endoscope device according to the fourth aspect, the control unit may measure the 3-dimensional shape of the specimen using only one pattern projection image by at least one of a spatial phase shift method, a Fourier transform method, a stripe order analysis and an optical cutting method.

According to a seventh aspect of the present invention, in the endoscope device according to the fourth aspect, the one period of the predetermined period may be a period of one second or more constituted by a first time width in a state in which the illumination light is emitted and a state in which emission of the projection light is stopped, and a second time width in a state in which emission of the illumination light is stopped and a state in which the projection light is emitted, and the second time width in the one period may be set to a sufficiently shorter time than one second.

According to an eighth aspect of the present invention, in the endoscope device according to the seventh aspect, the second time width may be set to a length of ⅕₂₅ of a second or less.

According to a ninth aspect of the present invention, in the endoscope device according to the seventh aspect, the second time width may be set to a length of ⅓₀ of a second or less.

According to a tenth aspect of the present invention, a measurement method of measuring a 3-dimensional shape of a specimen using an endoscope device, includes: periodically turning off illumination light at an interval of ⅕₂₅ of a second or less per second while an image of the specimen to which the illumination light is radiated is acquired; projecting a light and shade pattern on the specimen and acquiring a pattern projection image within a time in which the illumination light is turned off; measuring the 3-dimensional shape of the specimen using the pattern projection image after the pattern projection image is acquired; and displaying information obtained by the measurement of the 3-dimensional shape on the image acquired in a state in which the illumination light is radiated.

According to an eleventh aspect of the present invention, the measurement method according to the tenth aspect may further include: acquiring only one pattern projection image while the illumination light is in a turned-off state; and measuring the 3-dimensional shape of the specimen using the only one pattern projection image using at least one of a spatial phase shift method, a Fourier transform method, a stripe order analysis and an optical cutting method.

DESCRIPTION OF THE PREFERRED EMBODIMENTS

Hereinafter, an endoscope device and a measurement method in accordance with a preferred embodiment of the present invention will be described.

Figure 1:
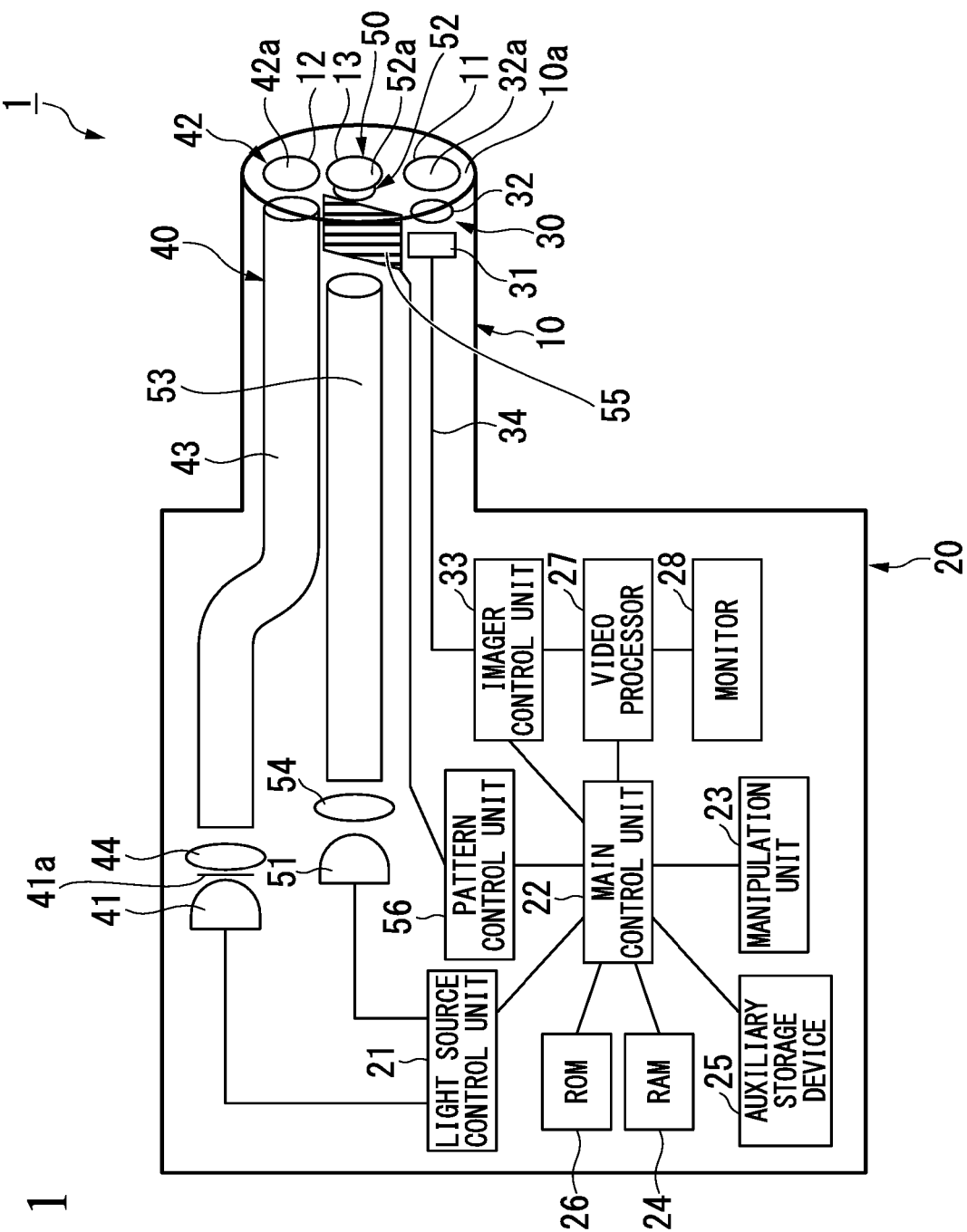
FIG. 1 is a block diagram showing a constitution of an endoscope device in accordance with a preferred embodiment of the present invention.
Figure 2:
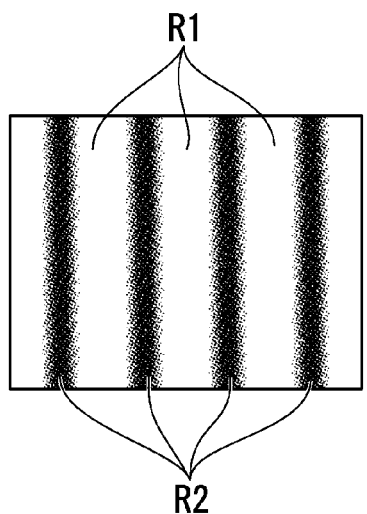
FIG. 2 is a schematic view showing a stripe pattern projected by the endoscope device in accordance with the preferred embodiment of the present invention.

First, a constitution of an endoscope device 1 in accordance with the preferred embodiment will be described. FIG. 1 is a block diagram showing the constitution of the endoscope device 1. FIG. 2 is a schematic view showing a light and shade pattern (a stripe pattern) projected by the endoscope device 1.

The endoscope device of the preferred embodiment is a measurement endoscope configured to measure a specimen using a pattern projection image formed by projecting a light and shade pattern on the specimen.

The endoscope device 1 is used for internal observation of the specimen, and observation of the specimen disposed at a position that a conventional observation apparatus cannot easily access. The endoscope device 1 includes a long insertion unit 10, and a main body section 20 to which a base end of the insertion unit 10 is connected.

As shown in FIG. 1, the insertion unit 10 is formed in a tubular shape. The insertion unit 10 is inserted into the specimen or an access path to the specimen. An imaging unit 30, an illumination unit 40 and a pattern projection unit 50 are installed at the insertion unit 10. The imaging unit 30 acquires an image of the specimen. The illumination unit 40 illuminates an observation field of vision in front of the insertion unit 10. The pattern projection unit 50 projects a light and shade pattern on the specimen. In the preferred embodiment, the pattern projection unit 50 projects a stripe pattern on the specimen as the light and shade pattern.

In addition, an opening 11, an illumination window 12 and a projection window 13 are installed at a tip surface 10a of the insertion unit 10. External light enters an object optical system 32 of the imaging unit 30 through the opening 11. The illumination window 12 radiates illumination light from the illumination unit 40 to a forward side of the insertion unit 10. The projection window 13 radiates stripes from the pattern projection unit 50 to a forward side of the insertion unit 10.

The imaging unit 30 includes an imager 31, the object optical system 32 and a imager control unit 33. The imager 31 is disposed in the vicinity of a tip of the insertion unit 10. The object optical system 32 is disposed in front of the imager 31. The imager control unit 33 is connected to the imager 31.

Various known constitutions including various kinds of image sensors such as a CCD, a CMOS, or the like, may be appropriately used as the imager 31.

The object optical system 32 is disposed in the opening 11 of the insertion unit 10. The object optical system 32 has a predetermined angle of view. The object optical system 32 allows the reflected light in the observation field of vision defined by the angle of view to enter the imager 31, and images an image of the specimen. In addition, the object optical system 32 has a cover member 32a having optical transparency. The cover member 32a seals the opening 11.

The imager control unit 33 is installed in the main body section 20. In addition, the imager control unit 33 is connected to the imager 31 by a wiring 34 extending in the insertion unit 10. The imager control unit 33 performs various kinds of controls such as driving of the imager 31, setting of acquiring a video signal, and so on.

The illumination unit 40 includes a first light source 41, an illumination optical system 42, a first fiber bundle 43 and a first incidence optical system 44. The first fiber bundle 43 guides light of the first light source 41 to the illumination optical system 42. The first incidence optical system 44 is disposed between the first light source 41 and the first fiber bundle 43.

The first light source 41 is a light source configured to emit white light. The first light source 41 is disposed in the main body section 20. A known light source such as a halogen lamp, a mercury lamp, or the like, may be appropriately selected and employed as the first light source 41. In the preferred embodiment, the halogen lamp is employed as the first light source 41. The light emitted from the first light source 41 is illumination light for illuminating the specimen. In addition, a shutter module 41a configured to switch an emission state of the illumination light is installed at the first light source 41. An operation of the shutter module 41a is controlled by a light source control unit 21 (which will be described below).

The illumination optical system 42 is attached to a tip of the insertion unit 10 or the vicinity of the tip. The illumination optical system 42 has a cover member 42a having optical transparency, and a lens group (not shown). The cover member 42a is installed in the illumination window 12 of the insertion unit 10. The illumination optical system 42 outputs the light radiated from the first light source 41 through the illumination window 12 to be spread to a field of vision range appropriate for the angle of view of the object optical system 32, and illuminates the entire observation field of vision.

The first fiber bundle 43 extends from the vicinity of the illumination optical system 42 to the vicinity of the first light source 41 in the main body section 20 through the insertion unit 10. The kind of the first fiber bundle 43 is not particularly limited but a general light guide may be used.

The first incidence optical system 44 converges the light emitted from the first light source 41 to substantially the same diameter as the first fiber bundle 43 and efficiently guides the light into the first fiber bundle 43.

The pattern projection unit 50 includes a second light source 51, a projection optical system 52, a second fiber bundle 53, a second incidence optical system 54 and a pattern generating unit 55. The second fiber bundle 53 guides the light of the second light source 51 into the projection optical system 52. The second incidence optical system 54 is disposed between the second light source 51 and the second fiber bundle 53. The pattern generating unit 55 is disposed on an optical path of the light emitted from the second light source 51.

The second light source 51 is a light source configured to emit different light from the first light source 41. The second light source 51 is disposed in the main body section 20. An LED light source, a laser light source, or the like, may be employed as the second light source 51. In the preferred embodiment, the LED light source is employed as the second light source 51. The light emitted from the second light source 51 is projection light configured to project the stripe pattern.

The projection optical system 52 is attached to the tip of the insertion unit 10 or the vicinity of the tip. The projection optical system 52 has a cover member 52a having optical transparency. The cover member 52a is disposed in the projection window 13 of the insertion unit 10. In addition, the cover member 52a installed at the projection window 13 may be configured in a lens shape. The projection optical system 52 spreads the light radiated from the second light source 51 to a field of vision range appropriate for the angle of view of the object optical system 32 and projects the light from the one projection window 13 into the observation field of vision.

The second fiber bundle 53 extends from the vicinity of the projection optical system 52 to the vicinity of the second light source 51 in the main body section 20 through the insertion unit 10. Like the first fiber bundle 43, a general light guide may be used as the second fiber bundle 53.

The second incidence optical system 54 converges the light emitted from the second light source 51 to substantially the same diameter as the second fiber bundle 53 and efficiently guides the light into the second fiber bundle 53.

The pattern generating unit 55 is configured to be formed in a stripe pattern. For example, a slit plate having a plurality of slits, or a transparent plate formed of glass, resin, or the like, on which a stripe pattern is drawn, may be used.

Moreover, the pattern generating unit 55 may use a liquid crystalline shutter module configured to switch penetration and non-penetration of the light to each element, a microelectromechanical system (MEMS) mirror module including a minute reflecting mirror installed at each element, or the like. In this case, since each element is individually controlled and a stripe pattern having an appropriate phase can be formed without movement of the entire pattern generating unit 55, a constitution of the pattern projection unit 50 can be simplified. Switching of the stripe pattern is performed by a pattern control unit 56 connected to the pattern generating unit 55.

The above-described imager control unit 33, the light source control unit 21 and a main control unit 22 are installed in the main body section 20. The light source control unit 21 controls an operation of emitting illumination light from the illumination unit 40 and an operation of emitting projection light from the pattern projection unit 50.

A video processor 27 and the main control unit 22 are connected to the imager control unit 33. The video processor 27 processes the video signal acquired by the imager 31. The main control unit 22 controls an operation of the imager control unit 33. The video processor 27 and the main control unit 22 are installed in the main body section 20.

A monitor (a display unit) 28 is connected to the video processor 27. The monitor 28 displays the video signal processed by the video processor 27 as an image.

The light source control unit 21 is connected to the first light source 41, the second light source 51 and the main control unit 22. The light source control unit 21 controls ON/OFF of the first light source 41 and the second light source 51 based on the control by the main control unit 22.

The main control unit 22 is further connected to a manipulation unit 23, a RAM 24, a ROM 26, an auxiliary storage device 25, and the pattern control unit 56.

The manipulation unit 23 has a switch or the like configured to allow a user to input various items into the endoscope 1.

In addition, a touch panel installed to overlap a display screen of the monitor 28 may be employed as the manipulation unit 23.

The RAM 24 functions as a work area used upon the imaging of the specimen, measurement of the 3-dimensional shape, or the like, using the endoscope 1.

For example, firmware or the like is recorded on the ROM 26. The ROM 26 is configured to read the firmware or the like upon starting of the endoscope 1.

As the auxiliary storage device 25, for example, a storage device, a magnetic storage device, or the like, having a nonvolatile memory, which is rewritable, may be employed.

Next, a constitution of the main control unit 22 will be described in detail.

The main control unit 22 blinks the first light source 41 and the second light source 51 with respect to the light source control unit 21 at a predetermined period W. The main control unit 22 reduces emission of the projection light from the second light source 51 in a state in which the illumination light is emitted from the first light source 41. The main control unit 22 controls emission of the projection light from the second light source 51 in a state in which emission of the illumination light from the first light source 41 is reduced. In the preferred embodiment, an example in which the main control unit 22 stops emission of the projection light from the second light source 51 will be described. However, if a user does not feel flicking, when the user looks the monitor 28, the main control unit 22 may be configured to reduce emission of the projection light from the second light source 51, rather than stopping the emission.

Figure 3:
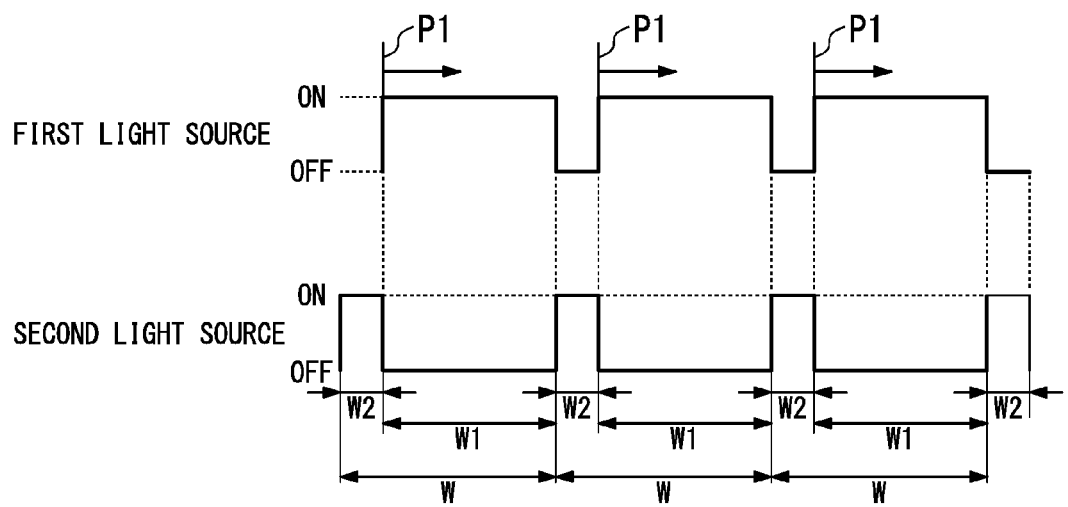
FIG. 3 is a timing chart showing emission timing of each light source and calculation timing of a 3-dimensional shape in use of the endoscope device in accordance with the preferred embodiment of the present invention.

FIG. 3 is a timing chart showing an emission timing of the first light source 41 and the second light source 51 and a calculation timing of a 3-dimensional shape in use of the endoscope device 1.

As shown in FIG. 3, one period W of a predetermined period, in which the first light source 41 and the second light source 51 blink, is constituted by a first time width W1 and a second time width W2. The first time width W1 is a state in which the illumination light is emitted and emission of the projection light is stopped. The second time width W2 is a state in which emission of the illumination light is stopped and the projection light is emitted.

In the preferred embodiment, the second time width W2 in the one period of the predetermined period W is set to a time in which flickering is not noticeable when the user who uses the endoscope device 1 looks the monitor 28.

Specifically, the predetermined period W is set to one second. That is, the second time width W2 in the period W of one second is set to a time sufficiently smaller than one second, for example, 1/30 of a second. Here, the first time width W1 is set to the remaining 29/30 of a second in the period W of one second.

In addition, according to a refresh rate of the monitor 28, the second time width W2 may be set to an appropriate time width of 1/30 of a second or less. For example, when the refresh rate of the monitor 28 is 60 fps, the second time width W2 is set to 1/60 of a second. Here, as the period is synchronized with the refresh rate of the monitor 28, omission of the image illuminated by the illumination light from the first light source 41 on the monitor 28 may be set to 1 frame/second.

Further, in the preferred embodiment, while the second time width W2 is set based on the number of frames (30 frames) per second of an NTSC format, the second time width W2 may be set based on the number of frames (25 frames) per second of a PAL format. Here, the second time width W2 is set to 1/25 of a second. In addition, the first time width W1 is set to 24/25 of a second.

In addition, in the preferred embodiment, the second time width W2 is set to a time in which at least one image can be appropriately acquired by the imaging unit 30. For example, in the preferred embodiment, a length of the second time width W2 is set to a length such that the imaging unit 30 can acquire one pattern projection image.

In addition, the main control unit 22 controls to acquire a light field image obtained by illuminating the illumination light on the specimen at the imaging unit 30 in a state in which the illumination light is emitted from the first light source 41. Further, the main control unit 22 controls to acquire a pattern projection image obtained by projecting a stripe pattern on the specimen at the imaging unit 30 in a state in which the projection light is emitted.

Specifically, the main control unit 22 controls to synchronize the predetermined period W with respect to the imager control unit 33 of the imaging unit 30 and image the image on the imager 31. The image imaged by the imager 31 is processed in the video processor 27. The image imaged when corresponding to the first time width W1 in the predetermined period W is extracted as a light field image by the main control unit 22. In addition, the image imaged when corresponding to the second time width W2 in the predetermined period W is extracted as a pattern projection image.

In this way, in the preferred embodiment, the image imaged by the imager 31 is divided into the light field image and the pattern projection image by the video processor 27.

The main control unit 22 measures a 3-dimensional shape using the pattern projection image extracted by the video processor 27. In addition, the main control unit 22 outputs the light field image extracted by the video processor 27 to the monitor 28.

In addition, the main control unit 22 may output the pattern projection image from the image imaged by the imager 31 to the monitor 28 without removing the pattern projection image. Even in this case, for example, when the time in which the pattern projection image is displayed on the monitor 28 is 1/30 of a second per second or less, flickering of the image on the monitor 28 is suppressed to an unnoticeable level.

The main control unit 22 can operate software for measuring a 3-dimensional shape of the specimen (hereinafter referred to as a "measurement program") using the pattern projection image acquired by the imaging unit 30. The main control unit 22 displays information obtained by the measurement using the pattern projection image on the monitor 28 as a light field image. In order to display the information obtained by the measurement using the pattern projection image on the monitor 28, when calculation by the measurement program is terminated, the main control unit 22 can output the information obtained by the measurement using the pattern projection image to the monitor 28 while overlapping the light field image or the pattern projection image displayed on the monitor 28.

Although this will be described below in detail, the measurement program is configured to terminate the calculation within the one period of the predetermined period W. Accordingly, display of the measurement result of the 3-dimensional shape is updated at the predetermined period W.

Figure 4:
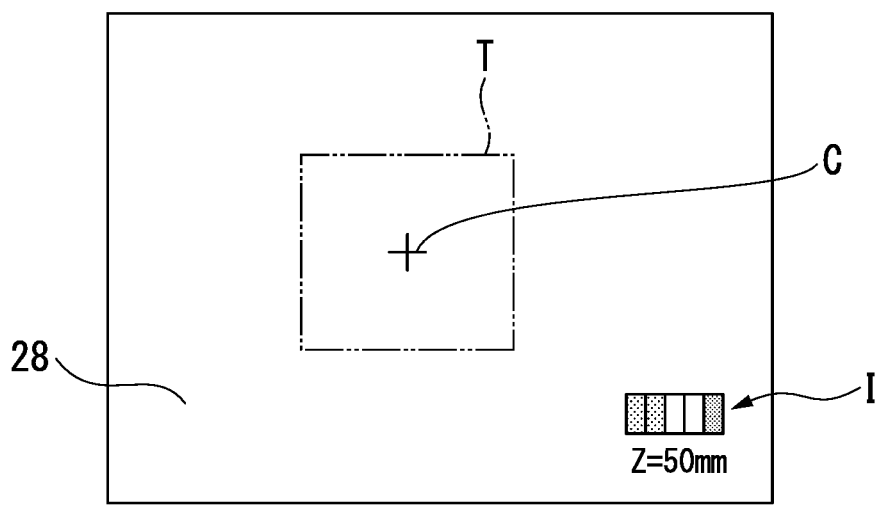
FIG. 4 is a schematic view showing a cursor and a target region displayed on a monitor in use of the endoscope device in accordance with the preferred embodiment of the present invention.
Figure 5:
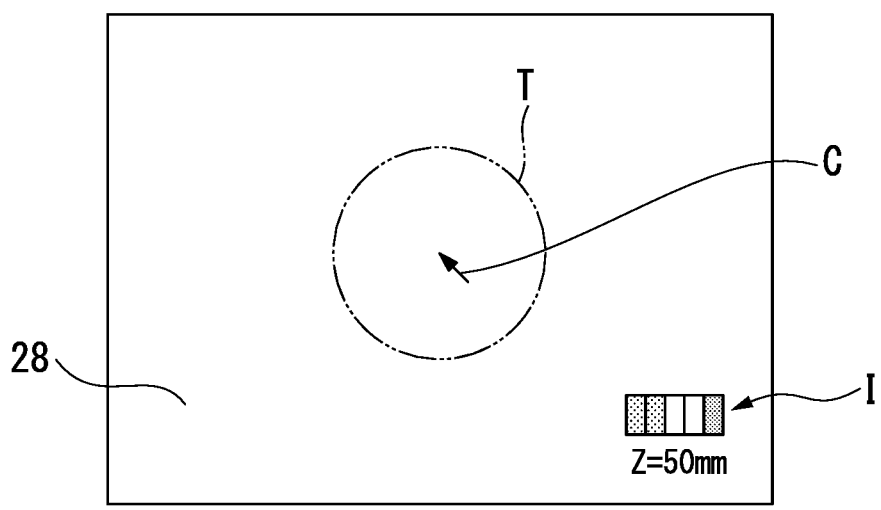
FIG. 5 is a schematic view showing a display example of the cursor and the target region displayed on the monitor in use of the endoscope device in accordance with the preferred embodiment of the present invention.

FIGS. 4 and 5 are schematic views showing display examples of a cursor C and a target region T displayed on the monitor 28 in use of the endoscope device.

As shown in FIGS. 4 and 5, the measurement program operated in the main control unit 22 displays the cursor C for determining a target region to measure the 3-dimensional shape of the specimen in the imaging field of vision of the imaging unit 30 on the monitor 28. The cursor C may have a shape enabling the user to easily designate coordinates or a region of the specimen, for example, a cross mark (see FIG. 4), an arrow mark (see FIG. 5), or the like. In addition, the cursor C may be used to designate an area of the target region with a shape of a circle mark, a rectangular frame, or the like. In this case, the measurement program may be configured such that a size of the cursor C can be varied by manipulation input of the user.

The measurement program sets the target region T for measuring the 3-dimensional shape on the monitor 28 based on the coordinates of the cursor C displayed on the monitor 28. For example, a predetermined region such as a rectangular shape or a circular shape is set as the target region T about a position of the cursor C designated as a specific position on the image such as the cross mark, the arrow mark, or the like.

In addition, the measurement program may be configured to vary a shape or a size of the target region T as well as a shape of the cursor C by the manipulation input of the user.

Further, the measurement program performs the calculation for measuring the 3-dimensional shape with respect to only the inside of the region set as the target region T for measuring the 3-dimensional shape.

The calculation by the measurement program uses at least one of a spatial phase shift method, a Fourier transform method, a stripe order analysis and an optical cutting method. The calculation using the spatial phase shift method, the Fourier transform method, the stripe order analysis and the optical cutting method is a calculation method that can measure the 3-dimensional shape of the specimen using only one pattern projection image.

The measurement program generates data of a calculation result showing the 3-dimensional shape in the target region T and data of measurement precision in the target region T, and stores the data, for example, on the RAM 24. Information showing a distance (an object distance) at least from the imaging unit 30 to the specimen is included in the data of the calculation result in the measurement program. In addition, information of quantification of at least a photographing state of the stripe pattern is included in the data of the measurement precision in the target region T.

As shown in FIGS. 4 and 5, information showing the object distance generated by the measurement program is displayed on the monitor 28 using a display method such as a numerical value, an indicator, or the like, as distance information I on the cursor C.

Alternatively, while not shown, distribution of the object distance in the target region T is displayed on a predetermined region in the monitor 28 as a color map or the like.

In this way, the main control unit 22 controls operations of the imaging unit 30, the illumination unit 40, the pattern projection unit 50, and the monitor 28.

Next, in the measurement method of the preferred embodiment, a method of measuring the specimen using the endoscope device 1 will be exemplarily described.

Figure 6:
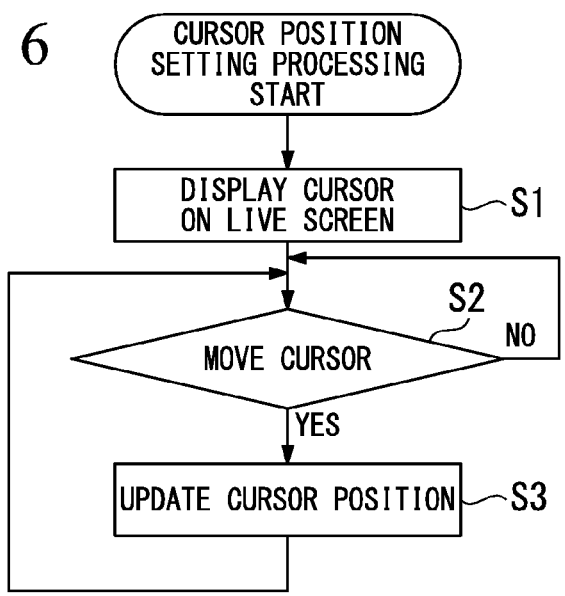
FIG. 6 is a flowchart for describing an operation in use of the endoscope device in accordance with the preferred embodiment of the present invention.
Figure 7:
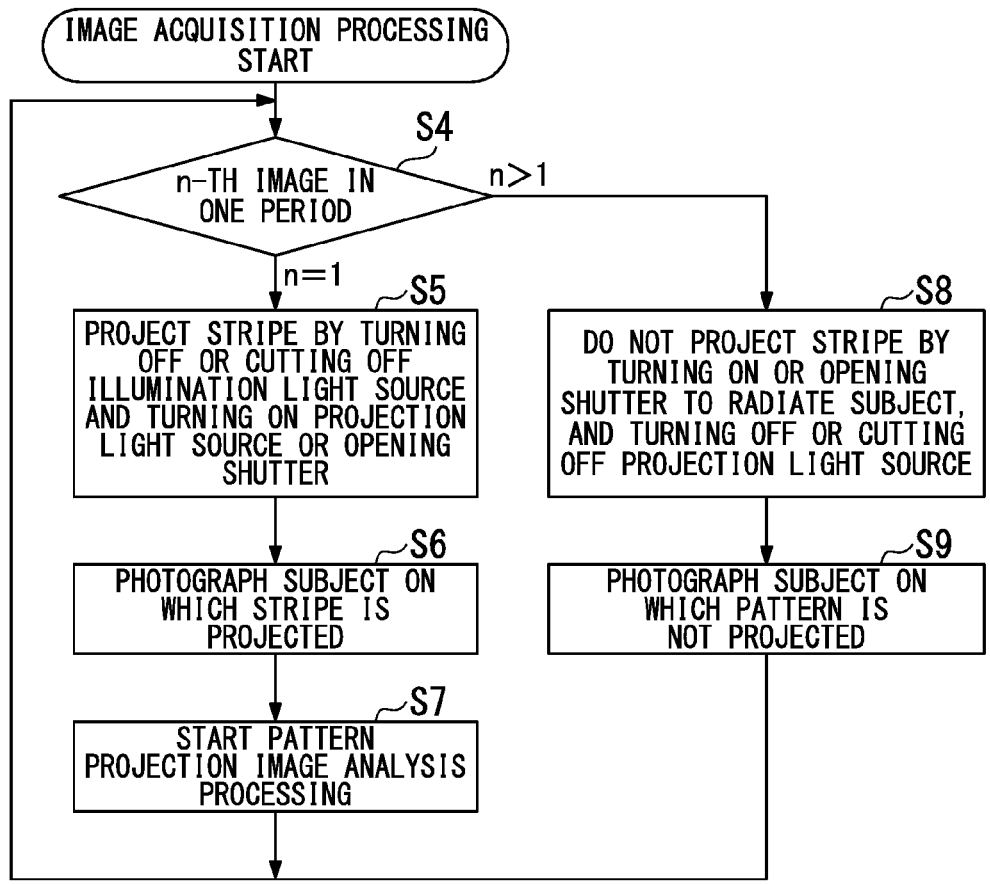
FIG. 7 is a flowchart for describing an operation in use of the endoscope device in accordance with the preferred embodiment of the present invention.
Figure 8:
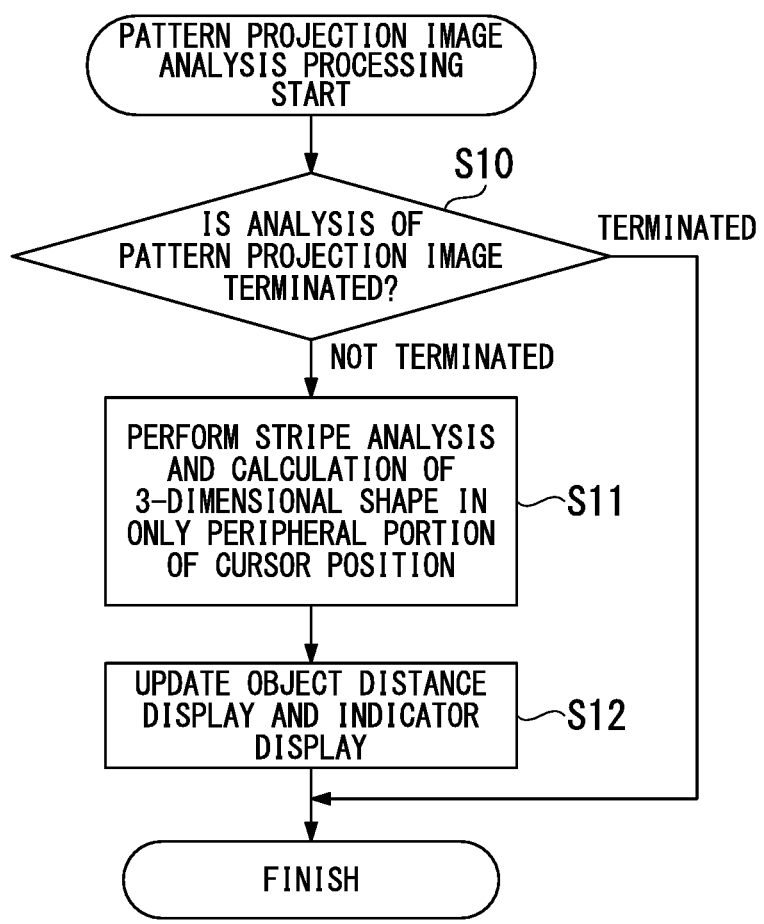
FIG. 8 is a flowchart for describing an operation in use of the endoscope device in accordance with the preferred embodiment of the present invention.

FIGS. 6 to 8 are flowcharts showing operations of measuring the 3-dimensional shape of the specimen using the endoscope device 1 in accordance with the preferred embodiment.

In the preferred embodiment, the endoscope device 1 includes an observation mode of performing observation only, rather than measurement of the 3-dimensional shape of the specimen, and a measurement mode of performing measurement of the 3-dimensional shape of the specimen. Hereinafter, detailed description of the operation in the observation mode will be omitted, and the operation in the measurement mode will be described in detail.

When the measurement mode is started, the measurement program is started and initialized. The measurement program generates a table that can reduce a calculation amount upon measurement, for example, a table related to parameters and solutions, and so on, in an equation that can be previously calculated, in calculations needed for measurement of the 3-dimensional shape, and temporarily stores the table on the RAM 24. In addition, the table may be previously stored on the ROM 26 or the auxiliary storage apparatus 25. In this case, the measurement program transmits the table stored on the ROM 26 or the auxiliary storage apparatus 25 to the RAM 24 and uses the table.

In addition, in the preferred embodiment, the measurement program is configured to perform parallel processing of cursor positioning processing, image acquisition processing, and pattern projection image analysis processing.

FIG. 6 is a flowchart of the cursor positioning processing. Step S1 shown in FIG. 6 is a step of displaying the cursor C on a live screen displayed on the monitor 28.

In step S1, the measurement program is set such that the cursor C is displayed on the monitor 28 and the user of the endoscope device 1 can move a position of the cursor C. In addition, the measurement program may fix the cursor C to a predetermined position on the monitor 28 (for example, a center of the monitor 28 or the like).

Based on the coordinates of the cursor C on the monitor 28, the target region T is set.

Here, step S1 is terminated and step S2 is performed.

Step S2 is a step of determining whether or not the cursor C is moved.

In step S2, it is detected that there is an input of moving the cursor C by the user of the endoscope device 1, or the like. The input of moving the cursor C may include mechanically detecting that there is an input operation by a button or a joystick. In addition, variation of the coordinates of the cursor C may be detected by the input operation by the button or the joystick.

In step S2, an input standby state is maintained until the input of moving the cursor C or the like is provided, and when presence of the input is detected, step S3 is performed.

Step S3 is a step of updating the position of the cursor C.

In step S3, the position of the cursor C displayed on the monitor 28 is varied according to the input operation. In addition, the position of the target region T is also updated according to the position of the cursor C.

Here, step S3 is terminated and the processing returns to step S2.

FIG. 7 is a flowchart of the image acquisition processing. In the image acquisition processing, information of the position of the cursor C and the position of the target region T is used with reference to the information of the position of the cursor C and the position of the target region T obtained in the cursor positioning processing.

Step S4 shown in FIG. 7 is a step of determining how many images (frames) are acquired in the one period of the predetermined period W.

In step S4, n is counted up whenever the image is acquired in the one period, and n is reset to 1 in the next period after the one period is terminated and then counted up again.

When n=1 in step S4, step S5 is performed, and when n is greater than 1 in step S4, step S8 is terminated.

Step S5 is a step of projecting a stripe pattern on the specimen within a time in which emission of the illumination light is stopped.

In step S5, when the illumination light is emitted from the first light source 41, the main control unit 22 controls the light source control unit 21 to stop emission of the illumination light upon completion of the first time width W1. As a method of stopping the emission of the illumination light, electrical connection to the first light source 41 may be stopped to turn off the first light source 41. In addition, the illumination light may be blocked by the shutter module 41a installed at the first light source 41. When the emission of the illumination light is stopped, the illumination light is not radiated to the specimen.

Further, the main control unit 22 controls the light source control unit 21 to start the emission of the projection light from the second light source 51. Here, the electrical connection state to the second light source 51 may be switched, and the shutter module may be installed at the second light source 51 to switch the emission state.

In the case of the preferred embodiment, since the LED light source is employed as the second light source 51, the light quantity can be stabilized for a sufficiently short time even when the shutter module is not provided.

As shown in FIG. 3, the time in which the projection light is emitted from the second light source 51 is the second time width W2 smaller than the first time width W1. For example, in the preferred embodiment, since the predetermined period W is one second and the second time width W2 is ⅓₀ of a second, when the second light source 51 is turned on/off as the electrical connection state of the second light source 51 itself is switched, power needed to emit light from the second light source 51 can be largely reduced.

In step S5, the projection light emitted from the second light source 51 passes through the pattern generating unit 55. Accordingly, as shown in FIG. 2, a bright section R1 is generated by the projection light that arrives at the specimen, and a dark section R2 is generated at an area at which the projection light is blocked by the pattern generating unit 55. As a result, the stripe pattern in which the bright section R1 and the dark section R2 are alternately arranged is projected on the specimen.

Here, step S5 is terminated and step S6 is performed.

Step S6 is a step of acquiring an image (a pattern projection image) of the specimen on which the stripe pattern is projected.

In step S6, the imaging unit 30 acquires the image of the specimen through the same operation as the operation of acquiring the light field image. In step S6, since the stripe pattern rather than the illumination light is projected on the specimen, the image acquired by the imaging unit 30 becomes the pattern projection image. In the preferred embodiment, only one pattern projection image is acquired in the second time width W2.

In step S6, the main control unit 22 extracts the one pattern projection image from the image processed in the video processor 27, and temporarily stores the pattern projection image on the RAM 24.

Here, step S6 is terminated and step S7 is performed.

Step S7 is a step of initializing the pattern projection image analysis processing.

In step S7, after the pattern projection image analysis processing (to be described below) is started, the processing returns to step S4.

Step S8 is a step of stopping projection of the stripe pattern on the specimen and emitting the illumination light.

In step S8, the main control unit 22 stops emission of the projection light from the second light source 51 upon completion of the second time width W2, controls the light source control unit 21 upon starting of the first time width W1, and starts emission of the illumination light from the first light source 41.

As a method of starting emission of the illumination light, electrical connection to the first light source 41 may be started to turn on the first light source 41. In addition, the shutter module 41*a* installed at the first light source 41 may be opened to emit the illumination light.

When a time from starting of the lighting of the first light source 41 until the light quantity of the first light source 41 is stabilized is sufficiently short, turning on and of the first light source 41 can be controlled, and power consumed by the first light source 41 can be reduced.

In addition, when the illumination light is blocked by the shutter module 41*a*, since there is no need to vary the light quantity emitted from the first light source 41 itself, a light source having a relatively long time in which the light quantity of the illumination light is stabilized may be employed.

In the case of the preferred embodiment, the halogen lamp employed as the first light source 41 corresponds to a light source having a relatively larger time in which the light quantity of the illumination light is stabilized. For this reason, an emission state of the illumination light is varied by an opening/closing operation of the shutter module 41*a*. Accordingly, variation in light quantity in the first time width W1 can be suppressed.

Here, step S8 is terminated and step S9 is performed.

Step S9 is a step of acquiring an image (a light field image) obtained by radiating the illumination light to the specimen.

In step S9, based on the control by the main control unit 22, the imaging unit 30 acquires one light field image within the first time width W1 in the predetermined period W, and displays the light field image on the monitor 28 through the video processor 27.

Here, step S9 is terminated and the processing returns to step S4. Next, during the first time width W1 in the predetermined period W, acquisition of the light field image is repeated in step S8 and step S9.

FIG. 8 is a flowchart of the pattern projection image analysis processing. The pattern projection image analysis processing is started using the issuance of an order of starting the pattern projection image analysis processing in the above-described step S7 in the image acquisition processing as a trigger.

Step S10 shown in FIG. 8 is a step of determining whether or not analysis of the stripe image is terminated.

In step S10, it is determined whether or not analysis or calculation for measurement of the 3-dimensional shape with respect to the pattern projection image acquired in step S6 is terminated.

When the analysis of the pattern projection image is not terminated, S11 is performed.

Step S11 is a step of measuring the 3-dimensional shape of the specimen using one pattern projection image.

In step S11, the measurement program measures the 3-dimensional shape of the specimen using at least one of a spatial phase shift method, a Fourier transform method, a stripe order analysis and an optical cutting method. Here, the measurement program uses only one pattern projection image. In the preferred embodiment, the measurement program performs stripe analysis, and performs calculation for measurement of the 3-dimensional shape using a table stored on the RAM 24.

In the preferred embodiment, the calculation can be performed in a shorter time than in the method of performing the calculation without using the table.

In addition, in step S11, the measurement program performs the measurement of the 3-dimensional shape using only the inside of the target region T as a target with reference to position information of the target region T acquired in the cursor positioning processing. In the preferred embodiment, the calculation can be performed in a shorter time than in the method of performing the calculation through the entire region of the image. The calculation result by the measurement program is temporarily stored on the RAM 24 with data showing measurement precision in the target region T. In addition, the calculation result by the measurement program may be stored on the auxiliary storage apparatus 25 in addition to the RAM 24. Further, when the measurement precision in the target region T is poor, data of the calculation result and the measurement precision may be discarded.

Here, step S11 is terminated and step S12 is performed.

Step S12 is a step of displaying the calculation result on the monitor 28.

In step S12, any one of the light field images in the image set (for example, the light field image acquired before acquisition of the pattern projection image) and information based on the calculation result is output to the monitor 28. In the monitor 28, for example, the calculation result may be displayed to overlap the light field image. As an example of displaying the calculation result, for example, a numerical value of the object distance or display of the indicator is updated.

In addition, the data of the measurement precision in the target region T can be displayed on the monitor 28. In this case, when the data of the calculation result and the measurement precision are discarded in step S11, characters or codes showing that the measurement precision is poor can be displayed on the monitor 28.

Here, step S12 is terminated.

The cursor positioning processing, the image acquisition processing, and the pattern projection image analysis processing shown in FIGS. 6 to 8 are performed in parallel as so called multi-task processing. The image acquisition processing and the pattern projection image analysis processing can receive interruption of the manipulation input or the like by the user.

For example, when the interruption that stops the display of the calculation result is generated due to the manipulation input or the like by the user, switching of the illumination light and the projection light in the predetermined period W can be stopped, and the illumination light can be constantly radiated.

Alternatively, when the manipulation for transition to the manipulation screen through which the user can measure a length between the two designated points or display the 3-dimensional shape throughout a larger range than that of the target region T is performed, after the pattern projection image is acquired, transition to the screen is performed.

As flows shown in steps S4, S5, S6 and S7 are repeated at a predetermined period, the imaging unit 30 acquires the pattern projection image at the beginning of the predetermined period. Otherwise, as the flows shown in steps S4, S8 and S9 are repeated at the predetermined period, the imaging unit 30 acquires a plurality of light field images without acquisition of the pattern projection image.

As the one period of the predetermined period W is terminated, a new period W is started as shown in FIG. 3, and the pattern projection image and the light field image are acquired by the above-described series of processes.

In addition, when the calculation amount in step S11 is large, the case in which the calculation cannot be terminated in the predetermined period W is also considered. In this case, the calculation is forcedly terminated, and new calculation using the next image set is performed.

The user of the endoscope device 1 can interrupt the measurement program and call another program when the 3-dimensional shape outside the target region T designated using the cursor C is measured, when the measurement is more precisely performed than that of the 3-dimensional shape using the measurement program, or when another measurement is performed.

Here, even when the other calculation method different from the calculation method using the measurement program is used, when it is determined that the measurement precision is poor in the latest information of the information showing the measurement precision, the fact may be displayed on the monitor 28, or the program may be prohibited to be switched to a program using another calculation method. Accordingly, photographing of the specimen can be prompted to the user under conditions in which the measurement precision cannot be easily decreased.

As described above, according to the endoscope device 1 and the measurement method of the preferred embodiment, whether the condition is appropriate for the measurement is determined in a short time. For this reason, since the measurement precision is smaller than required measurement precision, probability of the measurement failing can be suppressed.

In addition, as waste of time due to failure of the measurement is suppressed, utilization of the endoscope device 1 can be improved. This is specifically increased in efficiency when the measurement having a long calculation time in the program is performed.

Further, since the emission of the illumination light is periodically stopped, the pattern projection image is acquired when the illumination light is not emitted, and the light field image is acquired to be displayed on the monitor 28 when the illumination light is emitted, the 3-dimensional shape of the specimen can be measured in substantially real time while observing the specimen.

Furthermore, as the second time width W2 in which the image is acquired using the projection light is set to ⅟30 of a second or less in the period W set to one second, omission of the light field image displayed on the monitor 28 can be suppressed to a level that cannot be recognized by the user.

In addition, since the target region T is set to a portion of the region that can be imaged by the imaging unit 30 to measure the 3-dimensional shape with respect to only the inside of the target region T, the user can precisely measure the region needed for measurement of the 3-dimensional shape within a limited time.

Further, since the endoscope device 1 of the preferred embodiment can measure the distance from the imaging unit 30 to the specimen using the pattern projection image, there is no need to install a distance sensor at the insertion unit 10. For this reason, in the endoscope device 1 of the preferred embodiment, the insertion unit 10 can be reduced in diameter.

(Variant)

Next, a variant of the endoscope device 1 and the measurement method of the above-described preferred embodiment will be described.

In the variant, a constitution of the main control unit 22 is distinguished from the preferred embodiment in that processing in the case in which the insertion unit 10 and the specimen are relatively moved to cause positional deviation between the light field image and the pattern projection image is further performed.

The main control unit 22 includes a blur detection unit configured to select at least two images from the light field image and the pattern projection image and detect a blur between the insertion unit 10 and the specimen based on a deviation amount of the two selected images.

A threshold value of a deviation amount allowed in the two images is previously stored in the blur detection unit.

The blur detection unit detects a deviation amount of two images using a known unit. When the deviation amount of the two images exceeds the threshold value, the blur detection unit determines that there is a relative movement (blur) between the insertion unit 10 and the specimen.

In the preferred embodiment, the blur detection unit detects the blur between the insertion unit 10 and the specimen using the light field image acquired immediately before acquisition of the pattern projection image and the light field image acquired immediately after the acquisition thereof.

In addition, the main control unit 22 temporarily stores the light field image initially acquired in the first time width W1 and the light field image finally acquired in the first time width W1 on the RAM 24.

Further, in the variant, the pattern projection image is also temporarily stored on the RAM 24. The two light field images and the one pattern projection image temporarily stored on the RAM 24 are used for blur detection (to be described below) as an image set of three images.

Next, an operation of the endoscope device 1 of the variant and the measurement method of the variant will be described.

Figure 9:
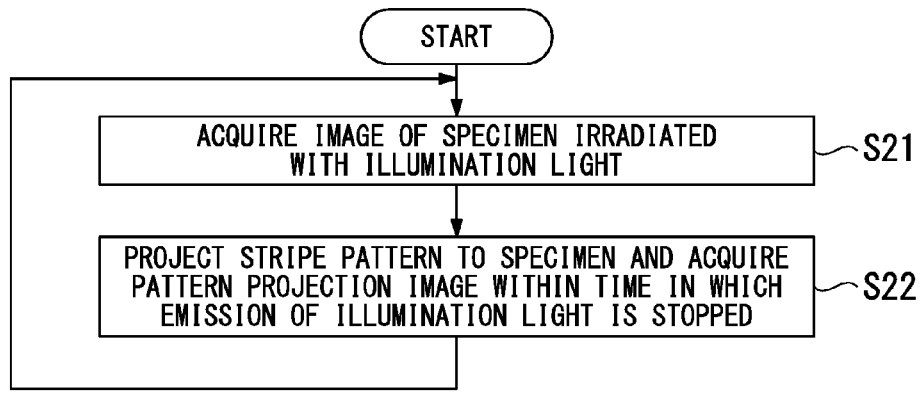
FIG. 9 is a flowchart for describing an operation in use of the endoscope device in accordance with the preferred embodiment of the present invention.
Figure 10:
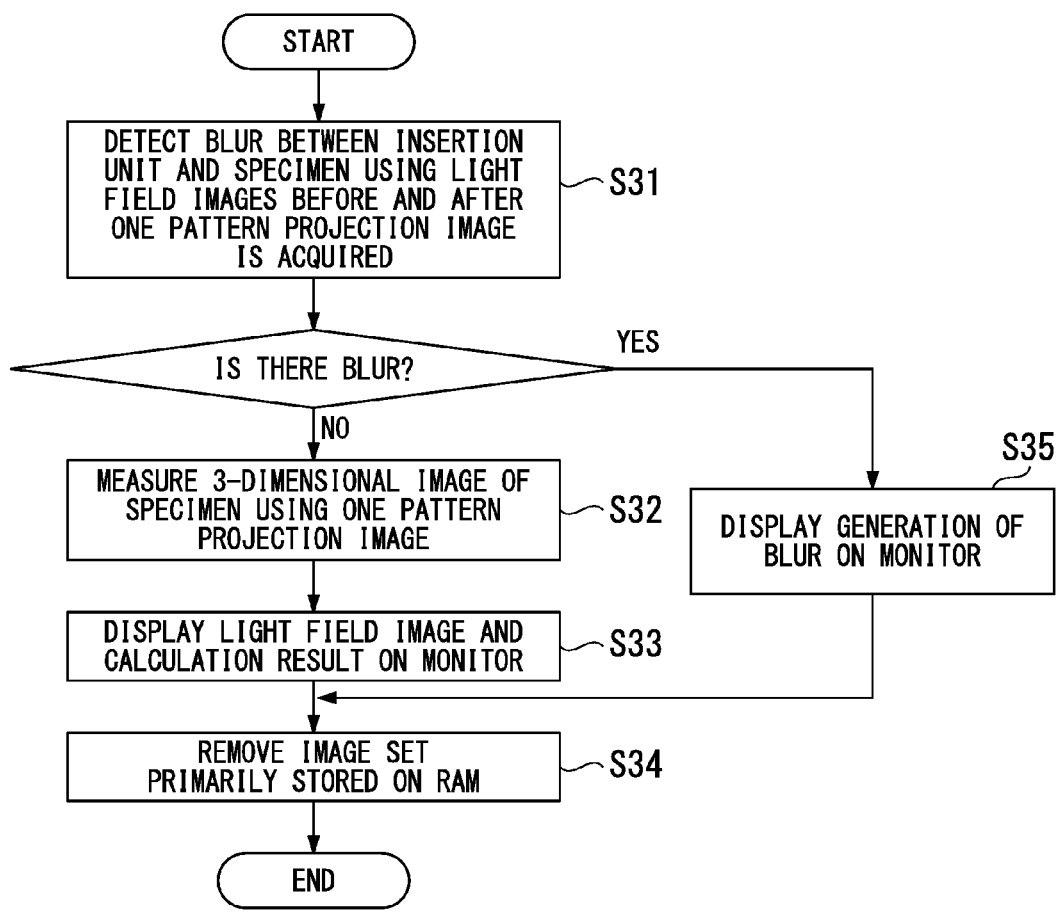
FIG. 10 is a flowchart for describing an operation in use of an endoscope device of a variant in accordance with the preferred embodiment of the present invention.

FIG. 9 is a flowchart showing an operation of acquiring an image of the specimen in the operation of measuring the 3-dimensional shape of the specimen using the endoscope device 1. FIG. 10 is a flowchart showing an operation of the measurement program for measuring the 3-dimensional shape using the pattern projection image of the specimen in the operation of measuring the 3-dimensional shape of the specimen using the endoscope device 1.

As shown in FIG. 9, in the variant, the light field image is acquired (step S21), and then the pattern projection image is acquired (step S22). The endoscope device 1 sequentially repeats step S21 and step S22 in this order until the interruption for terminating the measurement mode is input. As step S21 and step S22 are repeated, the image set of three images can be obtained. The image set of three images is constituted by one pattern projection image and light field images before and after (upon completion of the first time width W1 and upon starting of the first time width W1 of the next period).

The image set is temporarily stored on the RAM 24.

Next, an operation of the measurement program using the pattern projection image extracted in step S22 will be described with reference to FIG. 10.

Step S31 shown in FIG. 10 is a step of detecting the blur between the insertion unit 10 and the specimen using the light field images before and after the one pattern projection image is acquired.

Step S31 is initiated upon storage of the image set on the RAM 24 as a trigger. That is, as shown by reference character P1 of FIG. 3, step S31 is started when one light field image is acquired after the second time width W2 is terminated and the first time width W1 is started to acquire the pattern projection image.

In step S31, when it is determined that the deviation amount of the light field images before and after the one pattern projection image is less than the threshold value, step S32 is performed. In addition, in step S31, when it is determined that there is a deviation amount equal to or larger than the threshold value in the light field image before and after the one stripe image, step S35 is performed.

Step S32 shown in FIG. 10 is a step of performing the same processing as the above-described step S11.

Step S33 shown in FIG. 10 is a step of performing the same processing as the above-described step S12.

Step S34 shown in FIG. 10 is a step of removing the image set temporarily stored on the RAM 24.

As the image set is removed in step S34, a storage region is obtained to store a new image set. In addition, when the RAM 24 has a sufficient storage region, for example, the image set may be removed at a several-minute interval in a lump without removing the image set in step S34 at a predetermined period interval.

Further, the image set and the calculation result may be related and stored on the auxiliary storage apparatus 25. Accordingly, for example, even when the power of the endoscope device 1 is cut, when the endoscope device 1 is started again, the result can be obtained without re-measurement of the 3-dimensional shape in the image set acquired in the past.

Here, step S34 is terminated.

Step S35 is a step of displaying generation of the blur on the monitor.

In step S35, characters or codes showing the generation of the blur are displayed on the monitor 28.

Here, step S35 is terminated and step S34 is performed.

Even in the endoscope device and the measurement method of the variant, the same effect as in the above-described preferred embodiment will be exhibited.

In addition, since the blur detection unit is provided, when the specimen and the insertion unit 10 are deviated and a positional deviation occurs between the pattern projection image and the light field image, the measurement of the 3-dimensional shape is not performed. Accordingly, probability of displaying the object distance or the like, which is a wrong value, of the specimen displayed on the light field image due to the positional deviation can be reduced.

Hereinabove, while the preferred embodiment of the present invention has been described with reference to the accompanying drawings, a specific constitution is not limited to the preferred embodiment but may be design-changed without departing from the spirit of the present invention.

For example, when calculation performance of the main control unit is substantially high, the calculation for measurement of the 3-dimensional shape through the entire region of the imaging field of vision of the imaging unit can be completed within the one period. In addition, when the time of the one period is set to a time longer than one second described in the above-described preferred embodiment, for example, 10 seconds, while promptness is degraded, measurement of the dimensional shape can be performed with higher precision or with respect to a wide region.

Further, the measurement program may set an added region outside the target region to increase the measurement precision of the 3-dimensional shape in the target region, measure the 3-dimensional shape with respect to the target region and the added region, and then output only the measurement result of the 3-dimensional shape in the target region.

In addition, when the calculation for measurement of the 3-dimensional shape cannot be terminated within a predetermined period, instead of forced termination of the calculation and new calculation, calculation of a new image set may be started after completion of the calculation of the image set in continuation.

Further, in a step of detecting the blur, the blur can be detected using one light field image and one pattern projection image. In this case, since there is no need to acquire a plurality of light field images, a series of processes can be terminated in a shorter time.

In addition, in the above-described preferred embodiment, while an example using the light field image acquired upon completion of the first time width and upon starting of a first time width of the next period has been described as an example of the light field image used for detection of the blur, an acquisition timing and the number of acquired images of the light field images used for detection of the blur are not limited thereto. Only the light field image acquired before acquisition of the pattern projection image or only the light field image acquired after acquisition of the pattern projection image can be used.

In addition, in the above-described preferred embodiment, while an example in which the measurement program is software has been described, hardware such as LSI of measuring the 3-dimensional shape of the specimen using the pattern projection image acquired by the imaging unit may be used. Whether the software is used or the hardware is used may be appropriately selected according to a processing speed or a mounting cost.

According to the endoscope device and the measurement method of the preferred embodiment of the present invention, whether the condition is appropriate for the measurement can be determined in a short time.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. An endoscope device configured to measure a specimen using a pattern projection image of the specimen on which a light and shade pattern of light is projected, the endoscope device comprising:
   an imaging unit configured to acquire an image of the specimen;
   an illumination unit having a first light source configured to emit illumination light to illuminate an observation field of vision of the imaging unit;
   a pattern projection unit having a second light source configured to emit projection light to project the light and shade pattern on the specimen;
   a display unit configured to display the image acquired by the imaging unit; and
   a control unit configured to control the imaging unit, the illumination unit, the pattern projection unit, and the display unit,
   wherein the control unit:
   varies an emission state of the illumination light from the first light source at a predetermined period,
   reduces emission of the projection light from the second light source in a state in which the illumination light is emitted from the first light source,
   emits the projection light from the second light source in a state in which emission of the illumination light from the first light source is reduced,
   controls the imaging unit to acquire the pattern projection image obtained by projecting the light and shade pattern on the specimen in a state in which the projection light is emitted,
   controls the imaging unit to acquire a first light field image obtained by illuminating the specimen with the illumination light in a state in which the illumination light is emitted before the acquisition of the pattern projection image,
   controls the imaging unit to acquire a second light field image obtained by illuminating the specimen with the illumination light in a state in which the illumination light is emitted after the acquisition of the pattern projection image,
   detects a deviation amount between the first light field image and the second light field image,
   determines whether or not the deviation amount is less than a predetermined threshold value,
   measures a 3-dimensional shape of the specimen using the pattern projection image acquired by the imaging unit only when it is determined that the deviation amount is less than the threshold value, and
   displays information obtained by the measurement on the display unit with one of the first light field image and the second light field image.

2. The endoscope device according to claim 1, wherein the control unit further:
   displays a cursor used to determine a region in which the 3-dimensional shape of the specimen is measured in an imaging field of vision of the imaging unit on the display unit,
   sets the region on the display unit based on coordinates of the cursor, and
   measures the 3-dimensional shape of the corresponding specimen in the region.

3. The endoscope device according to claim 1, wherein the control unit measures the 3-dimensional shape of the specimen using only one pattern projection image by at least one of a spatial phase shift method, a Fourier transform method, a stripe order analysis and an optical cutting method.

4. The endoscope device according to claim 1, wherein the one period of the predetermined period is a period of one second or more constituted by a first time width in a state in which the illumination light is emitted and a state in which emission of the projection light is stopped, and a second time width in a state in which emission of the illumination light is stopped and a state in which the projection light is emitted, and
   the second time width in the one period is set to a sufficiently shorter time than one second.

5. The endoscope device according to claim 4, wherein the second time width is set to a length of $1/25$ of a second or less.

6. The endoscope device according to claim 4, wherein the second time width is set to a length of $1/30$ of a second or less.

7. An endoscope device configured to measure a specimen using a pattern projection image of the specimen on which a light and shade pattern of light is projected, the endoscope device comprising:
   an imaging unit configured to acquire an image of the specimen;
   an illumination unit having a first light source configured to emit illumination light to illuminate an observation field of vision of the imaging unit;
   a pattern projection unit having a second light source configured to emit projection light to project the light and shade pattern on the specimen;
   a display unit configured to display the image acquired by the imaging unit; and
   a control unit configured to control the imaging unit, the illumination unit, the pattern projection unit, and the display unit,
   wherein the control unit:

varies an emission state of the illumination light from the first light source at a predetermined period, reduces emission of the projection light from the second light source in a state in which the illumination light is emitted from the first light source, emits the projection light from the second light source in a state in which emission of the illumination light from the first light source is reduced, controls the imaging unit to acquire the pattern projection image obtained by projecting the light and shade pattern on the specimen in a state in which the projection light is emitted, controls the imaging unit to acquire a first light field image obtained by illuminating the specimen with the illumination light in a state in which the illumination light is emitted before the acquisition of the pattern projection image, controls the imaging unit to acquire a second light field image obtained by illuminating the specimen with the illumination light in a state in which the illumination light is emitted after the acquisition of the pattern projection image, detects a deviation amount between the first light field image and the second light field image, determines whether or not the deviation amount is less than a predetermined threshold value, and when it is determined that the deviation amount is not less than the threshold value, displays information regarding generation of a blur on the display unit without performing a measurement of a 3-dimensional shape of the specimen.

8. The endoscope device according to claim 7, wherein the control unit further:

displays a cursor used to determine a region in which the 3-dimensional shape of the specimen is measured in an imaging field of vision of the imaging unit on the display unit, sets the region on the display unit based on coordinates of the cursor, and measures the 3-dimensional shape of the corresponding specimen in the region.

9. The endoscope device according to claim 7, wherein the control unit measures the 3-dimensional shape of the specimen using only one pattern projection image by at least one of a spatial phase shift method, a Fourier transform method, a stripe order analysis and an optical cutting method.

10. The endoscope device according to claim 7, wherein the one period of the predetermined period is a period of one second or more constituted by a first time width in a state in which the illumination light is emitted and a state in which emission of the projection light is stopped, and a second time width in a state in which emission of the illumination light is stopped and a state in which the projection light is emitted, and the second time width in the one period is set to a sufficiently shorter time than one second.

11. The endoscope device according to claim 10, wherein the second time width is set to a length of $1/25$ of a second or less.

12. The endoscope device according to claim 10, wherein the second time width is set to a length of $1/30$ of a second or less.

* * * * *